(12) United States Patent
Cavanaugh et al.

(10) Patent No.: US 8,748,346 B1
(45) Date of Patent: Jun. 10, 2014

(54) COMPOSITION AND USE WITH CONTROLLED DROP APPLICATORS

(75) Inventors: Kevin Cavanaugh, Collierville, TN (US); Timothy B. Cartwright, Germantown, TN (US)

(73) Assignee: Floratine Products Group, Inc., Collierville, TN (US)

( * ) Notice: Subject to any disclaimer, the term of this patent is extended or adjusted under 35 U.S.C. 154(b) by 0 days.

(21) Appl. No.: 13/448,765

(22) Filed: Apr. 17, 2012

Related U.S. Application Data

(60) Provisional application No. 61/509,165, filed on Jul. 19, 2011.

(51) Int. Cl.
*A01N 43/38* (2006.01)
*A01N 43/08* (2006.01)
*A01P 21/00* (2006.01)

(52) U.S. Cl.
USPC .......................... 504/136; 504/196; 504/195

(58) Field of Classification Search
CPC ......... A01N 43/38; A01N 43/08; A01P 21/00
USPC .......................................... 504/136, 195, 196
See application file for complete search history.

(56) References Cited

U.S. PATENT DOCUMENTS

| 4,619,401 A | * | 10/1986 | Hardman | 239/214.17 |
| 5,188,655 A | * | 2/1993 | Jones et al. | 504/136 |
| 2006/0084573 A1 | * | 4/2006 | Grech et al. | 504/101 |

FOREIGN PATENT DOCUMENTS

WO  WO 2010116259   * 10/2010

* cited by examiner

*Primary Examiner* — Mina Haghighatian
(74) *Attorney, Agent, or Firm* — Harris Shelton Hanover Walsh, PLLC; Susan B. Fentress

(57) ABSTRACT

The present invention relates to the blending of key nutritional and hormonal components for successful application through a controlled drop applicator to satisfy plant requirements for growth. More specifically this invention provides a micronutrient composition for enhancing plant growth made of a mixture of gibberellic acid dissolved in triethanolamine. The gibberellic acids are: Gibberellic acid 4, Gibberellic acid 7, Gibberellic acid 9, Gibberellic acid 12. The gibberellic acids are mixed with kinetin dissolved in an alcohol; tryptophan dissolved in a humic acid solution; and a sufficient amount of a chelating agent.

5 Claims, No Drawings

COMPOSITION AND USE WITH CONTROLLED DROP APPLICATORS

CROSS-REFERENCE TO RELATED APPLICATIONS

This application claims the benefit of U.S. Ser. No. 61/509,165 filed Jul. 19, 2011 under 35 U.S.C. §119(e), hereby specifically incorporated by reference.

STATEMENT RE: FEDERALLY SPONSORED RESEARCH/DEVELOPMENT

Not applicable

BACKGROUND OF THE INVENTION

This invention is directed to liquid foliar hormonal products that are designed for use in low water volume sprayers. Foliar feeding of plants presents many technical challenges. Plants put up many barriers to the retention, entry, and transport of active agents such growth inhibitors and stimulators. In addition, environmental conditions and plant factors (age, architecture, leaf morphology and leaf arrangement) may decrease the activity of a plant modulator. Adjuvants are commonly used to improve a plant modulator performance.

The use of liquid fertilizers and hormonal blends, foliarly applied, on professionally managed turf is shown in U.S. Pat. No. 5,188,655. The '655 patent addresses the proper blends of gibberellic acids (GA), auxins (AUX) and cytokinins (CYT) to optimize plant growth. Proper blending of the hormonal components must be combined with proper application to the turf to ensure optimum growth and health. Therefore, all foliar products utilizing the stated hormonal blend must be used in traditional commercial sprayers that can maintain a recommended spray volume of 25-40 gallons per acre (GPA). A standard commercial spray rig has a 100 to 150 gallon tank mounted to the frame. This permits numerous nutritional and hormonal products to be added to the tank without incident because of the high degree of dilution.

But, based on the evidence of increasing environmental regulations, particularly water usage and runoff, manufacturers of spray rigs are redesigning their equipment to use ultra-low volumes of water. In some instances the equipment discharges water volumes in the 2-4 gibberellic acid range while tank sizes range from 8 to 14 gallons. This technology is known as the "Controlled Drop Applicator" (CDA). U.S. Pat. No. 4,619,401, provides an example of the newly designed spray nozzles that are required to provide these ultra-low water volumes. The design of these nozzles makes it imperative that the liquid formulations passing through this orifice do not contain rigid particulates or other components that will cause clogging. Because of the low-volume tanks and low spray rates, only one or two nutritional and hormonal products can be added at one time. However, as many as twenty different nutrients and hormones are needed for proper plant growth, thus multiple spray applications must be made to adequately cover the agronomic needs of the plant. This is not practical because of the demands of a golf course or sports stadium.

The manufacturers of liquid foliar fertilizers and hormonal products are now challenged to redesign their products to comply with the trend toward these ultra-low spray volumes. This is not a straight-forward exercise, as the chemical limitations do not allow concentrating these products by 10-fold. Furthermore, higher concentrations of products increase the likelihood of particulate formation and increased chance for clogging of the nozzles.

SUMMARY OF THE INVENTION

The present invention relates to the blending of key nutritional and hormonal components for successful application through a controlled drop applicator to satisfy plant requirements for growth. More specifically this invention provides a micronutrient composition for enhancing plant growth made of a mixture of gibberellic acid dissolved in triethanolamine. The gibberellic acids are: gibberellic acid 4, gibberellic acid 7, gibberellic acid 9, gibberellic acid 12. The gibberellic acids are mixed with kinetin dissolved in an alcohol; tryptophan dissolved in a humic acid solution; and a sufficient amount of a chelating agent.

This invention provides a micronutrient product made by the process involving solubilizing gibberellic acid in triethanolamine wherein the weight percentage of triethanolamine ranges from between 94-89% and the gibberellic acid ranges from between 6-11%; solubilizing kinetin in isopropyl alcohol wherein the weight percentages of said isopropyl alcohol ranges from between 85-95% and kinetin ranges from between 50-15%; and solubilizing tryptophan in a humic acid solution.

This invention also provides a method to provide plant nutritional product via controlled drop applicator. This method includes the steps of providing the composition to turf grass wherein the amount of gibberellic acid ranges from between 1-10 grams per acre; the amount of kinetin ranges from between 1-10 grams per acre; and the amount of tryptophan ranges from between 3 to 5 grams per acre.

DETAILED DESCRIPTION OF THE INVENTION

The present invention may be understood more readily by reference to the following detailed description of the invention. It is to be understood that this invention is not limited to the specific devices, methods, conditions or parameters described herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The present invention relates to the blending of nutritional and hormonal components for successful application through a controlled drop applicator to satisfy plant requirements for growth. Raw materials used for the source of individual hormones and nutrients must be more concentrated as are the final products themselves. Further, to accomplish these requirements the micronutrients have been:

1) solubilized with atypical solvents,
2) chelated in novel ways, and
3) correct ratios of hormones.

Solubilization. Micronutrient compounds containing iron, manganese, zinc, copper, and molybdenum are very soluble in water and do not require new or different means of dissolution. However, these compounds require special chelating technology to remain in solution.

The hormone balance containing gibberellins, auxins and cytokinins requires novel ways to enhance solubility. There are approximately 115 different gibberellic acids throughout the plant kingdom, but only a few of these promote proper growth in turf-grass. Specifically, GA4, GA7, GA9 and GA12 are crucial to cell division and controlled growth. However, these gibberellic acids have different solubilities in water and are much more difficult to keep in solution at the concentrations needed for controlled drop applicator products. The total of all four gibberellic acids listed above must be between 1 and 10 grams per acre of product sprayed.

This invention includes not only the proper blend of these gibberellic acids but also the solvent that can dissolve all four. Of the 1-10 gram total dosage per acre the hormonal blend of gibberellic acid contains:
GA4 40-50%
GA7 20-30%
GA9 10-20%
GA12 5-10%

This combination of gibberellic acids can only be sufficiently solubilized by a dilute solution of triethanolamine (TEA). The proper ratio of triethanolamine to gibberellic acid for complete solubility is:
triethanolamine (85% purity) 94-89%
gibberellic acid 6-11%

The historical source of cytokinins and auxins has been seaweed extract. However, the key components from the seaweed source are miniscule when compared to the amino acid and sugar content. To achieve the desired levels of these hormones, this invention incorporates the use of a singular cytokinin source and a singular auxin source.

Kinetin, the primary component of cytokinins, must be present in the product to provide between 1 and 10 grams per acre of the product sprayed. Proper solubility of the kinetin can best be achieved by dissolving in a dilute solution of isopropyl alcohol (IPA). The proper weight percentages for the kinetin and isopropyl alcohol in the solution are:
Isopropyl Alcohol (70% purity) 95-85%
Kinetin 5-15%

The source of auxin in this invention is tryptophan derived from casein. Tryptophan is an amino acid that serves as a ready precursor for the plant's conversion to either auxins—IAA or IBA. Tryptophan is difficult to get into solution. This invention utilizes a humic acid solution to achieve appropriate solubility. The equivalent auxin dosage to be sprayed per acre is between 3 and 5 grams. A solution of tryptophan is achieved when water, powdered casein, and a 20% solution of humic acid are mixed within these weight percentages:
Water 66-50%
Humic acid 29-42%
Casein 5-8%

Chelation. The primary purpose of chelation is to prevent the premature reaction of micronutrients in the spray tank. A chelating compound has multiple negative charges that bind with the positive charges of the nutrient. This chelated molecule is then absorbed foliarly into the plant and translocated to its metabolic site. If the chelating agent is too strong then the plant can't utilize it properly; if it is too weak then the chelating bonds could break in the spray tank making the nutrient hopelessly tied-up with other molecules. Ideally, the chelating agent should be a naturally occurring compound that the plant can easily metabolize and use in other plant functions—yet strong enough to protect the nutrient from other scavenging ions.

Chelating agents have been used extensively for years but selection of the proper agent depends on the intended use. Within the confines of this invention, the chelating agent should be natural and able to withstand the high concentration of other components in the product. Experience has shown, and demonstrated in this invention, that the following organic acids provide the most benefits when used to chelate these micronutrients
Iron—gluconic and fumaric acids
Manganese—glycolic and aconitic acids
Zinc—succinic and pyruvic acids
Copper—tartaric acid The addition rates for these organic acids must match the number of charges (negative to positive) and stoichiometry to properly chelate the nutrient. Prior art has utilized sugars or amino acids that have proven too weak or synthetically produced acids, such as EDTA, which are too strong. For example, iron gluconate, requires two molecules of gluconic acid to properly chelate one iron atom.

Hormonal Ratio

The hormonal ratio in product design depends on desired result in the plant. For instance, the desire to enhance root development requires a different hormonal balance than is required for topical growth and plant density. Therefore, this invention utilizes the following guidelines for hormonal ratios when designing a product:

| Hormone | Root Growth | Topical Growth |
| --- | --- | --- |
| gibberellic acid | 1 | 9 |
| tryptophan | 4 | 5 |
| CYT kinetin | 10 | 2 |

The ratio of gibberellic acid:tryptophan:kinetin is 9:5:2, for topical growth, while the ratio of gibberellic acid:tryptophan:kinetin is 1:4:10 for root growth. Variation from these ratios can result in abnormal growth or even senescence.

These and other aspects, features and advantages of the invention will be understood with reference to the detailed description herein, and will be realized by means of the various elements and combinations particularly pointed out in the appended claims. It is to be understood that both the foregoing general description and the following detailed description of the invention are exemplary and explanatory of preferred embodiments of the invention, and are not restrictive of the invention, as claimed.

The invention claimed is:

1. A micronutrient product made by the process comprising:
   solubilizing gibberellic acid in a sufficient amount of triethanolamine to form a solution of gibberellic acid and triethanolamine wherein the weight percentage of triethanolamine ranges from between 94-89% and the gibberellic acid ranges from between 6-11% for the solution of gibberellic acid and triethanolamine;
   solubilizing kinetin in a sufficient amount of isopropyl alcohol to form a solution of kinetin and isopropyl alcohol wherein the weight percentages of said isopropyl alcohol ranges from between 85-95% and kinetin ranges from between 50-15% for the solution of kinetin and isopropyl alcohol;

solubilizing tryptophan in a sufficient amount of a humic acid to form a solution of tryptophan and humic acid; and combining the solution of gibberellic acid and triethanolamine, the solution of kinetin and isopropyl alcohol and the solution of tryptophan and humic acid to make said micronutrient product.

2. The product of claim 1 wherein the humic acid is a solution and the humic acid solution is comprised of water, humic acid and casein and a volume percentage of the humic acid solution ranges from between 50-60% of water, 29-42% of humic acid and 5-8% of casein.

3. The micronutrient product of claim 1 wherein the ratio of gibberellic acid:tryptophan:kinetin is 9:5:2.

4. The micronutrient product of claim 1 wherein the ratio of gibberellic acid:tryptophan:kinetin is 1:4:10.

5. A method to provide a micronutrient product via a controlled drop applicator comprising the step of: applying the micronutrient product of claim 1 with a controlled drop applicator to turf grass wherein the amount of gibberellic acid ranges from between 1-10 grams per acre; wherein the amount of kinetin ranges from between 1-10 grams per acre; and wherein the amount of tryptophan ranges from between 3 to 5 grams per acre.

* * * * *